US010994097B2

(12) United States Patent
Ludwin et al.

(10) Patent No.: US 10,994,097 B2
(45) Date of Patent: May 4, 2021

(54) SYSTEM FOR INDICATING CATHETER DEFLECTION

(71) Applicant: BIOSENSE WEBSTER (ISRAEL) LTD., Yokneam (IL)

(72) Inventors: Doron Moshe Ludwin, Haifa (IL); Dror Levy, Irvine, CA (US); Yevgeny Bonyak, Haifa (IL); Mark Stanley, Seal Beach, CA (US)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 367 days.

(21) Appl. No.: 15/947,250

(22) Filed: Apr. 6, 2018

(65) Prior Publication Data

US 2018/0221624 A1    Aug. 9, 2018

Related U.S. Application Data

(63) Continuation of application No. 13/181,918, filed on Jul. 13, 2011, now abandoned.

(51) Int. Cl.
*A61M 25/00* (2006.01)
*A61M 25/01* (2006.01)
*A61B 1/005* (2006.01)
*A61B 1/00* (2006.01)

(52) U.S. Cl.
CPC ....... *A61M 25/0136* (2013.01); *A61B 1/0052* (2013.01); *A61B 1/0005* (2013.01); *A61B 1/0057* (2013.01); *A61M 25/0133* (2013.01); *A61M 2209/01* (2013.01)

(58) Field of Classification Search
CPC .......... A61M 25/0136; A61M 25/0133; A61B 1/0052; A61B 1/0057

USPC ...................................................... 604/95.04
See application file for complete search history.

(56) References Cited

U.S. PATENT DOCUMENTS

| | | |
|---|---|---|
| 4,930,494 A | 6/1990 | Takehana et al. |
| 5,462,527 A | 10/1995 | Stevens-Wright et al. |
| 5,542,434 A | 8/1996 | Imran et al. |
| 5,643,255 A | 7/1997 | Organ |
| 5,861,024 A | 1/1999 | Rashidi |
| 6,551,302 B1 | 4/2003 | Rosinko et al. |
| 7,465,288 B2 | 12/2008 | Dudney et al. |
| 7,682,358 B2 | 3/2010 | Gullickson et al. |

(Continued)

FOREIGN PATENT DOCUMENTS

| | | |
|---|---|---|
| CN | 1093933 A | 10/1994 |
| CN | 102000379 A | 4/2011 |

(Continued)

OTHER PUBLICATIONS

Extended European Search Report for European Application No. 12176163, dated Nov. 20, 2012, 9 pages.

*Primary Examiner* — Steven O Douglas
(74) *Attorney, Agent, or Firm* — Etan S. Chatlynne; Roberts Calderon Safran & Cole P C.

(57) ABSTRACT

Apparatus, consisting of a probe, having a proximal end and a distal end, which is deflectable in first and second directions. The apparatus includes a probe manipulator, which is coupled to the proximal end of the probe and has first and second tactile control elements. The elements are operable by a user of the probe to deflect the distal end in the first and second directions, respectively, and are tactilely distinguishable one from the other.

10 Claims, 6 Drawing Sheets

(56) References Cited

U.S. PATENT DOCUMENTS

| | | | |
|---|---|---|---|
| 7,914,440 B2* | 3/2011 | Otawara | A61B 1/00098 600/104 |
| 2003/0120195 A1 | 6/2003 | Milo et al. | |
| 2005/0096590 A1* | 5/2005 | Gullickson | A61M 25/0136 604/95.04 |
| 2005/0228274 A1 | 10/2005 | Boese et al. | |
| 2005/0277875 A1* | 12/2005 | Selkee | A61M 25/005 604/95.04 |
| 2006/0074297 A1* | 4/2006 | Viswanathan | A61B 34/70 600/424 |
| 2007/0233044 A1* | 10/2007 | Wallace | A61M 25/01 604/528 |
| 2008/0103520 A1 | 5/2008 | Selkee | |
| 2008/0255540 A1 | 10/2008 | Selkee | |
| 2009/0182269 A1 | 7/2009 | Selkee | |
| 2011/0152880 A1 | 6/2011 | Alvarez et al. | |

FOREIGN PATENT DOCUMENTS

| | | |
|---|---|---|
| EP | 0980693 A1 | 2/2000 |
| EP | 0980693 B1 | 1/2005 |
| EP | 2305115 A1 | 4/2011 |
| JP | H06292728 A | 10/1994 |
| JP | 2000102621 A | 4/2000 |
| JP | 2006015018 A | 1/2006 |
| JP | 2008190910 A | 8/2008 |
| JP | 2009527344 A | 7/2009 |
| JP | 2010253125 A | 11/2010 |
| WO | 9417856 A1 | 8/1994 |
| WO | 2007082216 A1 | 7/2007 |
| WO | 2009099464 A1 | 8/2009 |
| WO | 2011046874 A1 | 4/2011 |

* cited by examiner

SYSTEM FOR INDICATING CATHETER DEFLECTION

CROSS-REFERENCE TO RELATED APPLICATIONS

This application is a continuation of and claims priority to and the benefit of U.S. patent application Ser. No. 13/181,918, filed Jul. 13, 2011, the entire contents of which is incorporated herein by reference.

FIELD OF THE INVENTION

The present invention relates generally to catheter probes, and specifically to manipulation of the probes by an operator.

BACKGROUND OF THE INVENTION

Probes such as catheters may be inserted into the body of a patient during a medical procedure that is performed on the patient. The probes may be used for a variety of purposes, such as an internal inspection of the patient, or ablation of an organ of the patient.

The insertion of the probe into the patient is typically a delicate procedure, which needs to be performed carefully.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

SUMMARY OF THE INVENTION

An embodiment of the present invention provides apparatus, including:

a probe, having a proximal end and a distal end, which is deflectable in first and second directions; and a probe manipulator, which is coupled to the proximal end of the probe and includes first and second tactile control elements, which are operable by a user of the probe to deflect the distal end in the first and second directions, respectively, and which are tactilely distinguishable one from the other.

Typically, the first and second tactile control elements have respective first and second shapes, wherein the first and second shapes are different one from the other.

In a disclosed embodiment the first and second tactile control elements have respective first and second congruent shapes, wherein the first and second shapes are oriented differently.

In a further disclosed embodiment the first and second tactile control elements have respective surfaces which are tactilely distinguishable one from the other.

In a yet further disclosed embodiment the first and second tactile control elements are configured to have respective visible characteristics different one from the other.

In an alternative embodiment the apparatus includes a screen configured to display respective different graphic symbols in response to deflection of the distal end in the first direction and in the second direction. Typically, the first and second tactile control elements are configured to have respective visible characteristics different one from the other, and wherein the respective graphic symbols comprise the respective visible characteristics. The screen may be configured to display a further graphic symbol in response to the distal end being in an un-deflected state.

In a further alternative embodiment the first and second tactile control elements are related by 2-fold rotational symmetry.

There is further provided, according to an embodiment of the present invention, a method, including:

configuring a probe, having a proximal end, and a distal end that is deflectable in first and second directions; and coupling a probe manipulator to the proximal end of the probe, the manipulator including first and second tactile control elements, which are operable by a user of the probe to deflect the distal end in the first and second directions, respectively, and which are tactilely distinguishable one from the other.

The present disclosure will be more fully understood from the following detailed description of the embodiments thereof, taken together with the drawings, in which:

DETAILED DESCRIPTION OF EMBODIMENTS

Overview

Embodiments of the present invention provide a system that facilitates the manipulation of a probe having a distal end which is deflectable in two directions. Typically the two directions are opposite to each other, so that, for example, the distal end may be deflected to the left or to the right. A probe manipulator is coupled to the proximal end of the probe, and the manipulator is configured to have two control elements. Operation of one of the control elements deflects the distal end in one direction; operation of the other control element deflects the distal end in the other direction.

Typically, an operator using the manipulator to insert the probe into the body of a patient may need to twist the manipulator during or after the insertion, for example to locate the distal end in a desired position. Such a twist may cause the operator to confuse which control element causes which type of deflection, since the operator may typically rely on visible cues, such as the position of the control elements, to select which element to operate.

Embodiments of the present invention overcome this confusion by forming the control elements to be tactilely distinguishable from each other, so that the operator is able to select the required control element on the basis of touch or feel, rather than on the basis of visual cues.

System Description

Figure 1:
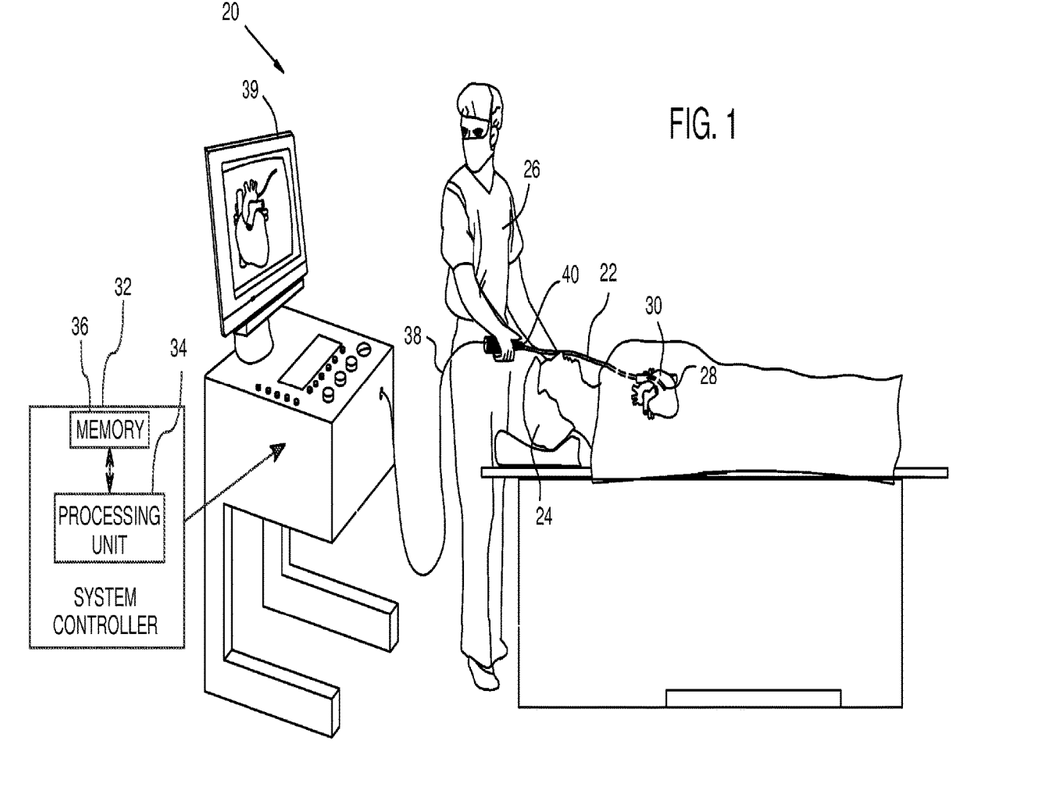
FIG. 1 is a schematic illustration of a system for indicating the deflection direction of a probe, according to an embodiment of the present invention.

Reference is now made to FIG. 1, which is a schematic illustration of a system 20 for indicating the deflection direction of a probe, according to an embodiment of the present invention. System 20 comprises a catheter probe 22 which is inserted into the body of a patient 24 during a medical procedure. The procedure is performed by an operator 26, typically a medical professional. By way of example, the procedure assumed in the description herein comprises insertion of a distal end 28 of the probe into a heart 30 of the patient. However, it will be understood that embodiments of the present invention are not limited to such a procedure, but rather may be used for any procedure requiring or using knowledge of the deflection direction of a probe.

Probe 22 typically comprises tracking elements in distal end 28 which enable system 20 to track the position and orientation of the distal end. For example, the position and orientation may be measured using coils in the distal end which detect levels of magnetic fields generated by magnetic field transmitters external to patient 24. Such a technique for measuring the position and location of the distal end is used in Carto system probes produced by Biosense Webster of Diamond Bar, Calif. Other techniques for tracking the position and orientation of the distal end, such as by using impedance measurements between electrodes on the distal end and one or more electrodes on the skin of patient 24, are known in the art. System 20 is assumed to use one or more of these techniques in order to measure the position and orientation of distal end 28. For simplicity and clarity, tracking elements within the distal end that are used to track the position and orientation are not shown in the diagram.

Signals from the tracking elements are processed by a system controller 32, comprising a processing unit 34 communicating with a memory 36. The signals transfer via a cable 38, connecting the tracking elements of probe 22, as well as other elements of the probe such as electrodes incorporated in the distal end, to the controller. The controller, under overall control of operator 26, uses software stored in memory 36 for analyzing the signals from the tracking elements, as well as to perform other functions related to the operation of system 20. Results of the operations performed by controller 32 are presented to the operator on a screen 39, which typically displays a graphic user interface to the operator, and/or an image of heart 30. The software may be downloaded to controller 32 in electronic form, over a network, for example, or it may, alternatively or additionally, be provided and/or stored on non-transitory tangible media, such as magnetic, optical, or electronic memory.

Probe 22 is configured so that operator 26 is able to deflect distal end 28 of the probe, while the probe is inserted into patient 24, in one of two directions. Such a bi-directionally deflectable probe and its operation is described in U.S. Patent Applications 2005/0277875 and 2008/0255540, both to Selkee, which are incorporated herein by reference. A bi-directionally deflectable probe system is also produced, as an EZ Steer Bi-Directional Catheter, by Biosense Webster. For clarity, in the description herein probe 22 is assumed to be constructed generally as described for the probe described in U.S. Patent Application 2008/0255540.

Probe 22 comprises a probe manipulator 40 which is mechanically connected to the proximal end of the probe. Operator 26 holds the manipulator and uses it in order to control entry and exit of the probe into and out of the patient, as well as to deflect the probe.

Figure 2:
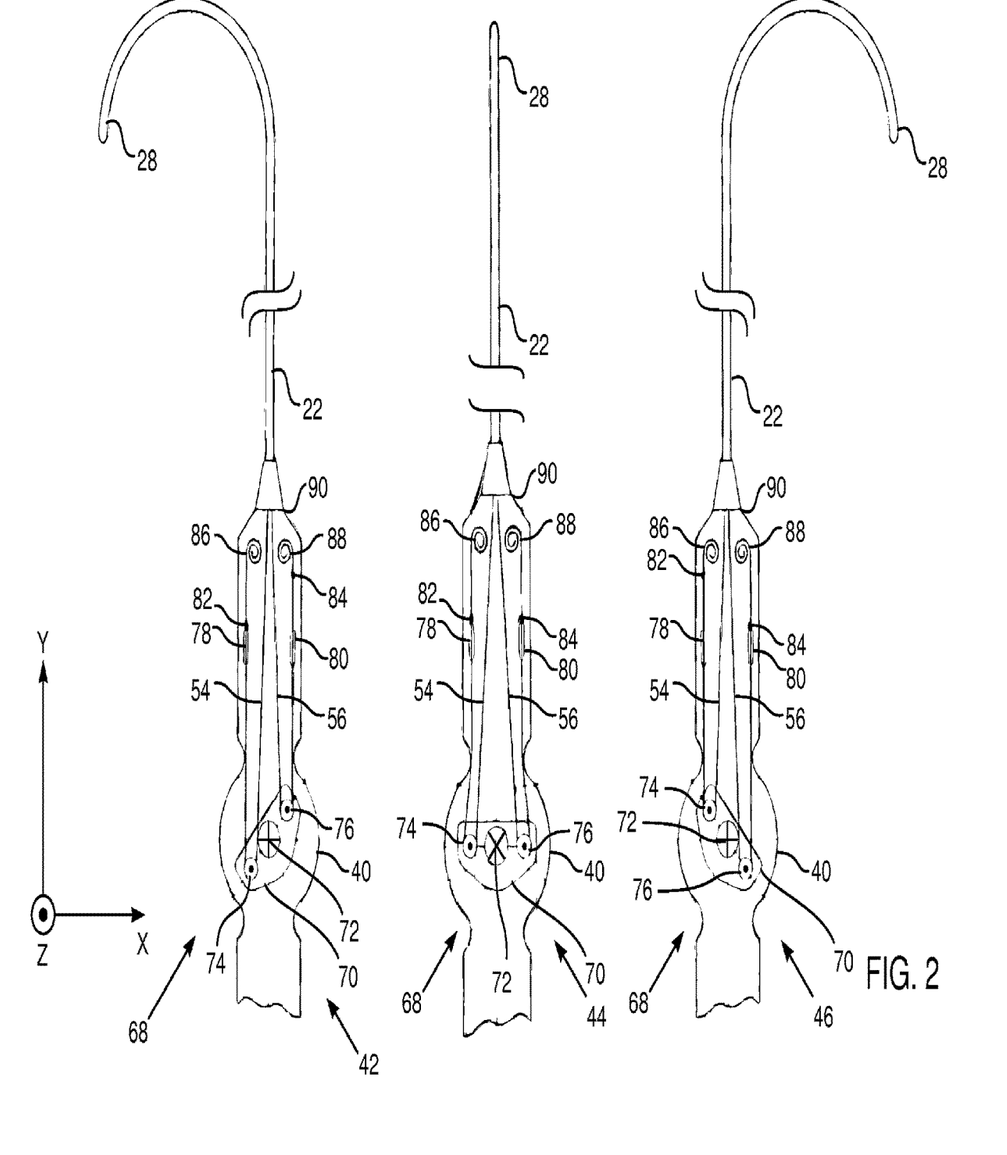
FIG. 2 is a schematic figure illustrating internal elements of a probe manipulator of the system, according to an embodiment of the present invention.
Figure 3:
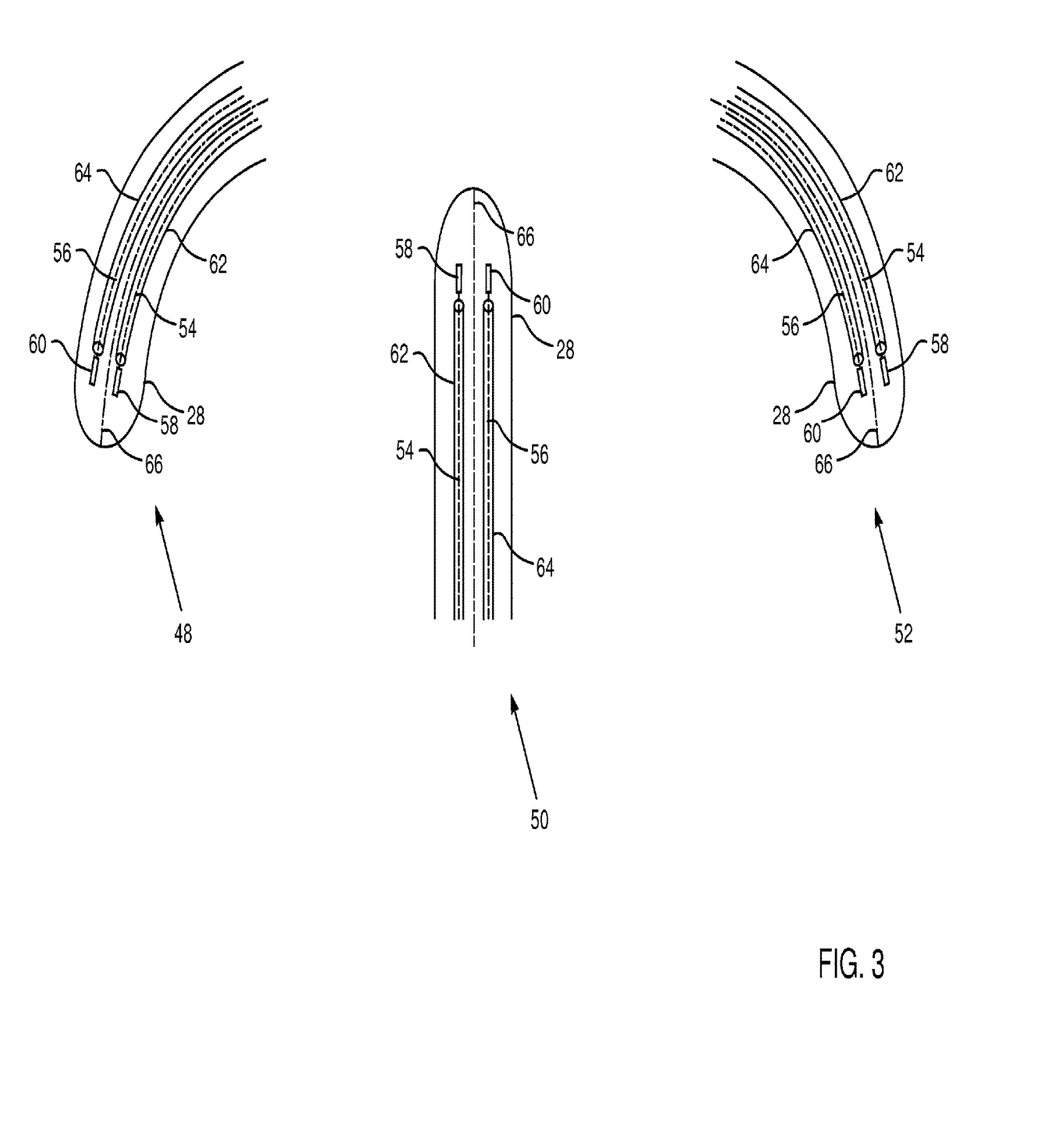
FIG. 3 is a schematic figure illustrating internal elements of a probe of the system, according to and embodiment of the present invention.

FIG. 2 is a schematic figure illustrating internal elements of manipulator 40, and FIG. 3 is a schematic figure illustrating internal elements of probe 22, according to embodiments of the present invention. For the following description with reference to FIGS. 2 and 3, a set of right handed orthogonal xyz axes are assumed to be attached to manipulator 40, probe 22 is assumed to extend in a positive y-direction from the manipulator, and the probe and the manipulator are assumed to lie generally in an x-y plane defined by the axes. It will be appreciated that the description herein applying the xyz axes described above is for the purposes of explanation only, and those having ordinary skill in the art will be able to adapt the explanation for other orientations of the probe and the manipulator.

Diagrams 42, 44, and 46 in FIG. 2 illustrate the probe manipulator when probe 22 is respectively deflected left, un-deflected, and deflected right. Diagrams 48, 50, and 52 in FIG. 3 respectively illustrate distal end 28 when it is deflected left, un-deflected, and deflected right. The deflection is in an x-y plane, and is assumed to be measured with respect to the y-axis. As shown in FIG. 3, probe 22 comprises a puller wire 54 and a puller wire 56 which are anchored at distal end 28 by respective anchors 58, 60. Wires 54 and 56 are constrained by respective generally parallel lumens 62, 64 within probe 22, the wires being able to slide within the lumens. Lumens 62 and 64 are typically approximately equidistant from, and symmetrically disposed with respect to, a central axis 66 of probe 22, and the axis and the lumens lie in, and may be considered to define, an x-y plane.

As shown in FIG. 2, wires 54 and 56 extend to a steering assembly 68 connected to manipulator 40. Steering assembly comprises a lever 70, which is able to rotate around an axis 72 parallel to the z-axis. Lever 70 comprises two pulleys 74, 76, around which wires 54 and respectively pass. After passing their respective pulleys, wires 54 and 56 traverse respective stops 78, 80, before being attached at their ends 82, 84 to springs 86 and 88.

In the un-deflected state, illustrated in diagrams 44 and 50, the lengths of wires 54 and 56 within probe 22, i.e., extending from a distal end 90 of manipulator 40, are approximately equal so that distal end 28 is not deflected from the y-axis. In the un-deflected state ends 82 and 84 are against their respective stops 78 and 80.

As illustrated in diagrams 42 and 48, distal end 28 has been deflected left. The left deflection is achieved by lever 70 rotating counter-clockwise from the system's un-deflected state. The rotation causes the length of wire 54 within probe 22, i.e., from end 90 to end 28, to be shorter than in the un-deflected state, since end 82 maintains contact with stop 78. The counter-clockwise rotation causes pulley 76 to move towards distal end 90, allowing the length of wire 56 within probe 22 to be longer than in the un-deflected state. (The movement of pulley 76 also allows spring 88 to retract wire 56, so that end 84 moves from its stop 80.) The combination within probe 22 of the reduction in length of wire 54, and the extension in length of wire 56, causes distal end 28 to deflect left.

Diagrams 46 and 52 illustrate distal end 28 deflected right, caused by lever 70 rotating clockwise from the system's un-deflected state. The lever rotation causes, within probe 22, wire 54 to be extended in length and wire 56 to be reduced in length. The combination of the two length changes causes distal end 28 to deflect right.

Figure 4:
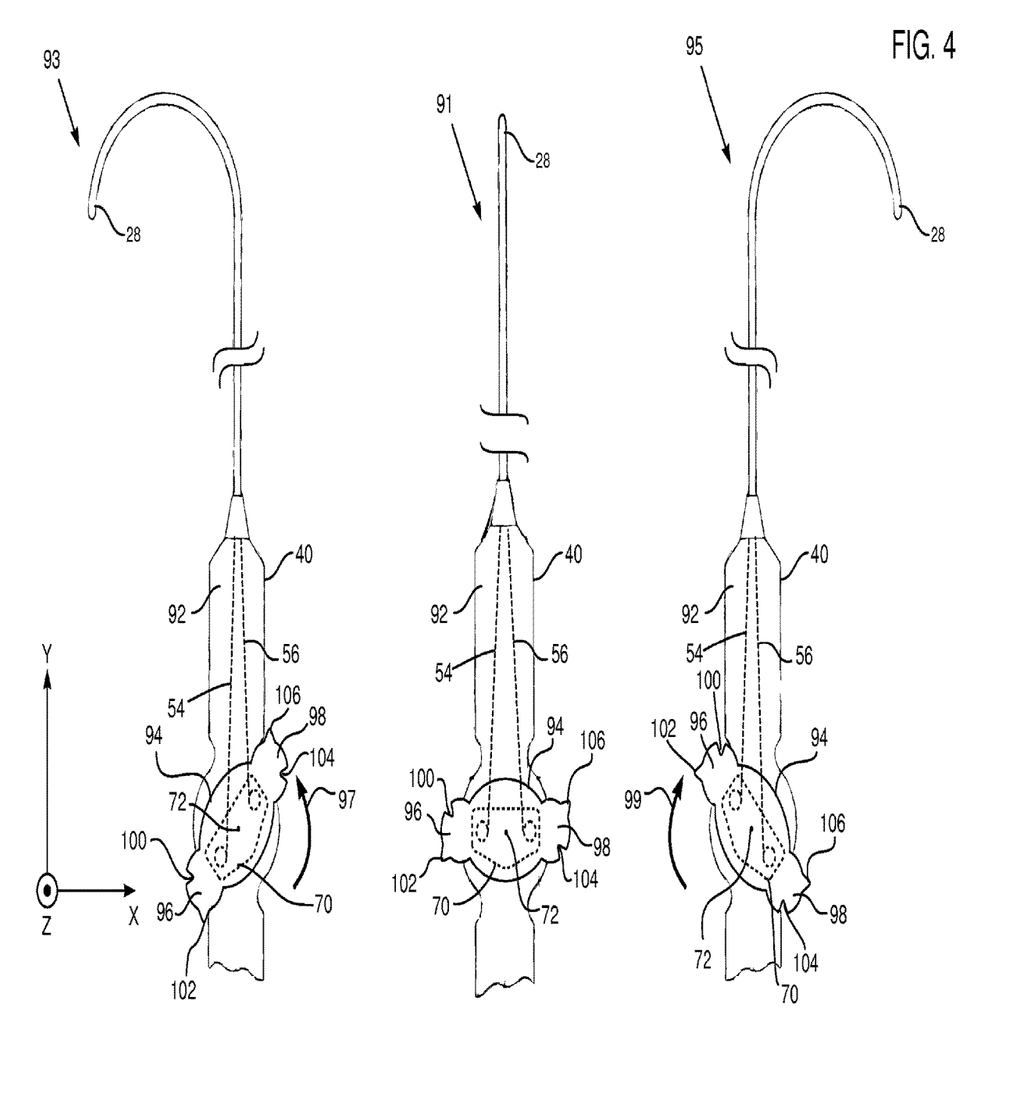
FIG. 4 is a schematic figure illustrating the probe manipulator in an assembled state, according to an embodiment of the present invention.

FIG. 4 is a schematic figure illustrating manipulator 40 in an assembled state, according to an embodiment of the present invention. In the assembled state, the internal elements of the manipulator are typically enclosed in a housing 92, so that the elements are not exposed. In addition, a control 94 is fixedly connected to lever 70 so that axis 72 is common to both the control and the lever. Control 94 is above housing 92. Operator 26 holds housing 92, and rotates lever 70 by pushing (or pulling) on end tactile control elements 96 or 98 of control 94.

A diagram 91 illustrates distal end 28 in an un-deflected state, and diagrams 93 and 95 show the distal end in a deflected state. Thus, as shown in diagram 93, rotating control 94 about axis 72 in the direction shown by arrow 97 deflects distal end 28 to the left. As shown in diagram 95, rotating control 94 about axis 72 in the direction shown by arrow 99 deflects the distal end to the right. From the point of view of an operator looking down on the manipulator, i.e., an operator above the plane of the paper, rotating control 94 in the direction shown in this view by arrow 97, i.e., counterclockwise, deflects the distal end to the left. Similarly, rotating control 94 shown in this view by arrow 99, i.e., clockwise, deflects the distal end to the right.

Figure 5:
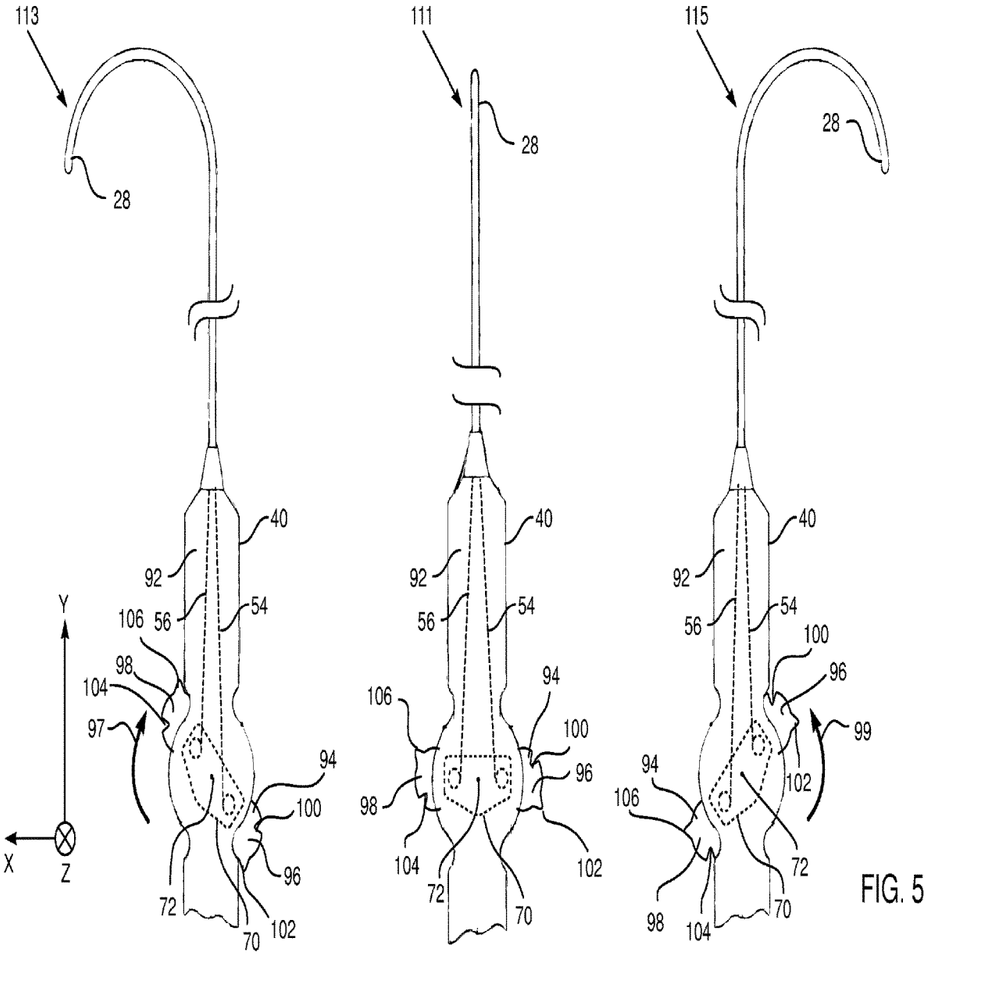
FIG. 5 is a schematic figure illustrating the manipulator in an assembled state, and rotated from the orientation of FIG. 4, according to an embodiment of the present invention.

FIG. 5 is a schematic figure illustrating manipulator 40 in an assembled state, and rotated from the orientation of FIG. 4, according to an embodiment of the present invention. Typically, while operator 26 operates probe 22 with manipulator 40, the operator may rotate the manipulator, for example around the y-axis. Such a rotation typically does not cause a corresponding rotation of probe 22, but rather generates a twist in the probe. Diagrams 111, 113, and 115 respectively correspond to diagrams 91, 93, and 95 (FIG. 4), and show the manipulator rotated by approximately 180° about the y-axis. In this case control 94 is below housing 92.

As is illustrated in diagram 115, in this view arrow now shows that control 94 needs to rotate counterclockwise to deflect the distal end to the right. Similarly, as shown in diagram 113, in this view arrow 97 now shows that control 94 needs to rotate clockwise to deflect the distal end to the left. Comparing the situations illustrated in FIGS. 4 and 5, it is apparent that rotation of manipulator 40 may confuse the operator as to the directions of deflection of the distal end caused by rotation of the left and right elements of control 94.

Embodiments of the present invention eliminate the confusion by causing the control elements to be tactilely distinguishable from each other. In other words, operator is able to distinguish between the elements by touching the elements, and by perceiving from the sense of touch that the elements are different. The operator is thus able to identify each of the elements by touch alone. By way of example, element 96 is assumed to have a groove 100 inset in the edge of the element and a protuberance 102 projecting from the edge of the element. As shown in the diagrams of FIGS. 4 and 5, in element 96 groove 100 has a greater y-value than protuberance 102. Also by way of example, element 98 is assumed to have a groove 104 inset in the edge of the element and a protuberance 106 projecting from the edge of the element. As shown in the diagrams, in element 98 groove 104 has a smaller y-value than protuberance 106. The different arrangements of grooves and protuberances in the two control elements provide different tactile feedback to operator 26 when the operator feels or touches the elements.

Typically, elements 96 and 98 are implemented to be tactilely distinguishable by arranging that the shapes of the elements are different, as in the example described above and illustrated in FIGS. 4 and 5. As another example, one tactile control element may have a smooth continuously curved edge with no sharp corners, and the other tactile control element may have a discontinuous smooth curved edge, with at least one sharp corner. Other differences in shapes for the two elements, enabling operator 26 to distinguish the elements on the basis of touch or feel, will be apparent to those having ordinary skill in the art. Such differences include, but are not limited to, the elements having congruent shapes, but being oriented differently, so that the different orientation is perceptible to operator 26 when the operator touches the elements.

In some embodiments, the tactile difference between the two elements may comprise implementing the surfaces of the elements to be different. For example, the surface of element 96 may be formed as a smooth surface, and the surface of element 98 may be rough. In this case the shapes and orientations of the two elements may be the same, and the tactile difference between the two elements is implemented by selecting one or more characteristics of the surface, such as the surface's roughness, elasticity, and/or thermal conductivity, to be different, so that the operator is able to detect the difference on touching the surfaces. In some embodiments, the shape and the surface of the two elements may be different.

In some embodiments, as well as forming elements 96 and 98 to be tactilely distinguishable, the elements are constructed so that they are visually distinguishable. For example, element 96 may have at least part of its surface colored blue, and element 98 may have at least part of its surface colored yellow. In some embodiments the visible differences between the elements may be implemented by selecting visual characteristics other than color of the elements to be different, such as by making one element transparent and one element opaque.

In some embodiments, the tactile differences between the two elements are configured to be related by 2-fold rotational symmetry. Such a configuration is shown in FIGS. 4 and 5, which illustrate that control 94 has 2-fold rotational symmetry about axis 72. With such 2-fold symmetry a tactile difference relationship within each of the control elements can be used as a "global" command for distal tip deflection. For example, as is demonstrated in the figures, the tactile difference relationship between the protuberances and the grooves means that following the instruction "rotate the protuberance towards the groove" deflects distal tip 28 right no matter how the manipulator is oriented. Such a global command may be provided to the operator in terms of a convenient mnemonic. E.g., if grooves 100 and 104 are termed dimples, and if protuberances 102 and 106 are termed pimples, then the mnemonic "rotate the pimple (protuberance) towards the dimple (groove) to deflect the tip right" applies regardless of the orientation of the manipulator, and regardless of which control element is considered.

Figure 6:
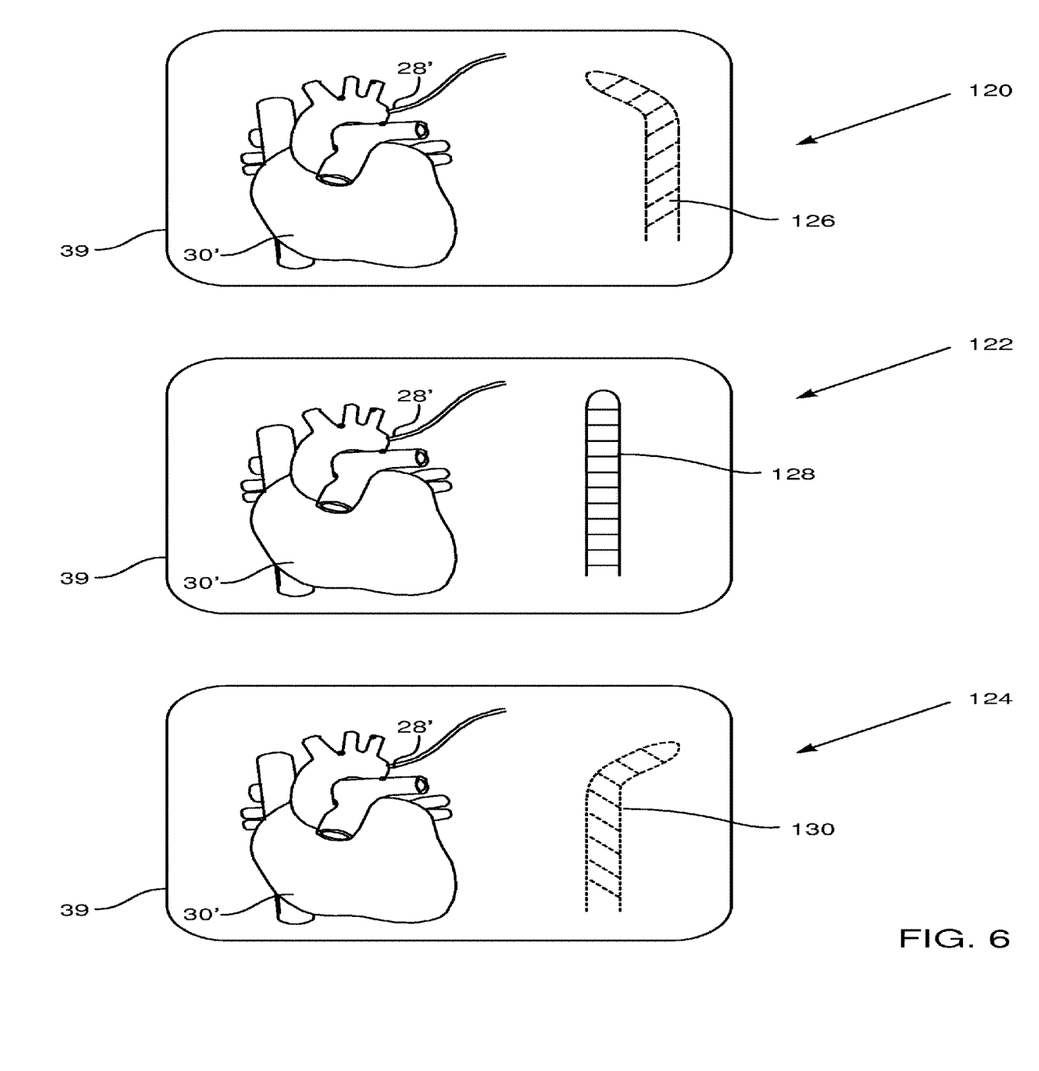
FIG. 6 is a schematic figure of a display of graphic symbols, according to an embodiment of the present invention.

FIG. 6 is a schematic figure of graphic symbols, according to an embodiment of the present invention. Typically, the location and orientation of distal end 28 within heart 30 is displayed on screen 39 using respective images 28' and 30'. In addition, graphic symbols representing the state of the distal end i.e., if it is deflected or un-deflected, may be presented on the screen in order to assist operator in manipulating the probe and its end. The graphic symbols provide a visual confirmation to the operator of the deflected or un-deflected state of end 28, as generated by the operator using manipulator 40. Diagrams 120, 122, and 124 illustrate symbols 126, 128, and 130 displayed on screen in the case of the distal end respectively being deflected left, being un-deflected, and being deflected right. Diagram 120, with symbol 126, corresponds to diagrams 113 and 93; diagram 122, with symbol 128, corresponds to diagrams 111 and 91; and diagram 124, with symbol 130, corresponds to diagrams 115 and 95 (FIGS. 4 and 5).

In the case of embodiments where the tactile control elements of control 94 have a visual characteristic, a corresponding visual characteristic may be applied to symbols 126, 128, and 130. For example, if at least part of element 96 is colored blue, then symbol 130 may be colored blue; and if at least part of element 98 is colored yellow, then symbol 126 may be colored yellow. Alternatively or additionally, the corresponding visual characteristic applied to symbols 126, 128, and 130 may comprise other visible qualities applied to the symbols, such as different types of shading, as exemplified in FIG. 6.

The description above has assumed a probe manipulator with one control for deflecting the probe, the control having separate tactile control elements which may be formed as part of a single integrated control. It will be understood that this is one example of a probe manipulator, and other manipulators may have tactile control elements which are separated from one another, and which are not formed as part of a single integrated control. It will also be understood that probe manipulators according to embodiments of the present invention do not need to be of the generally planar form exemplified above, but may comprise other geometric forms, such as a trackball or a joystick. All such manipulators are included within the scope of the present invention.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. A method for steering a medical device, comprising:
   receiving the medical device, the medical device comprising,
      an elongated and flexible probe having a longitudinal axis, a distal end and a proximal end, the distal end being deflectable from an undeflected position in a first direction and a second direction, and
      a manipulator proximal of the probe, the manipulator having a housing and a control having a first arm and a second arm, the first arm including a first tactile feature and a second tactile feature located distal of the first tactile feature;
   touching the first tactile feature and the second tactile feature;
   determining that movement of the control in a direction from the first tactile feature toward the second tactile feature moves the distal end of the probe in the first direction; and
   moving the control in the direction from the first tactile feature toward the second tactile feature.

2. The method of claim 1, further comprising:
   determining that movement of the control in a direction from the second tactile feature toward the first tactile feature moves the distal end of the probe in the second direction; and
   moving the control in the direction from the second tactile feature toward the first tactile feature.

3. The method of claim 1, wherein the second arm includes a third tactile feature and a fourth tactile feature located proximal of the third tactile feature, the method further comprising:
   touching the third tactile feature and the fourth tactile feature;
   determining that movement of the control in a direction from the third tactile feature toward the fourth tactile feature moves the distal end of the probe in the first direction; and
   moving the control in the direction from the third tactile feature toward the fourth tactile feature.

4. The method of claim 3, wherein the first arm includes a first visual characteristic and the second arm includes a second visual characteristic that is different from the first visual characteristic.

5. The method of claim 4, wherein the first visual characteristic is a transparent portion of the first arm and the second visual characteristic is an opaque portion of the second arm.

6. The medical device of claim 4, wherein the first visual characteristic is a first color and the second visual characteristic is a different color.

7. The method of claim 4, further comprising viewing a display showing an image of the distal end.

8. The method of claim 7, further comprising viewing a change to the image of the distal end corresponding to the first visual characteristic or the second visual characteristic.

9. The method of claim 7, wherein the first tactile feature is a groove, the second tactile feature is a protuberance, the third tactile feature is a groove and the fourth tactile feature is a protuberance.

10. The method of claim 9, wherein the first and second tactile features are related to the third and fourth tactile features by a 2-fold rotational symmetry.

* * * * *